United States Patent [19]

Welch et al.

[11] Patent Number: 4,614,434

[45] Date of Patent: Sep. 30, 1986

[54] DOUBLE MULTICHROMATIC PHOTOMETER WITH A SINGLE LIGHT-SOURCE AND A SINGLE DETECTOR, PARTICULARLY FOR PERFORMING CHEMICAL AND CLINICAL ANALYSES

[75] Inventors: Henry H. Welch; Corindo Felici, both of Rome, Italy

[73] Assignee: POLI-MAK S.p.A., Rome, Italy

[21] Appl. No.: 615,863

[22] Filed: May 31, 1984

[30] Foreign Application Priority Data

Feb. 21, 1984 [IT] Italy ................. 47723 A/84

[51] Int. Cl.$^4$ ................. G01J 3/51; G01N 21/31
[52] U.S. Cl. ................. 356/418; 250/575; 356/434
[58] Field of Search ................. 356/51, 408, 410, 414, 356/418, 434, 323, 325; 250/575, 343

[56] References Cited

U.S. PATENT DOCUMENTS

| | | | |
|---|---|---|---|
| 2,904,687 | 9/1959 | Sobcov et al. ................. | 250/343 X |
| 3,292,484 | 12/1966 | Clay ................. | 356/434 |
| 3,690,772 | 9/1972 | Endl ................. | 356/434 X |
| 3,941,487 | 3/1976 | Ehret et al. ................. | 356/414 X |

Primary Examiner—Vincent P. McGraw
Attorney, Agent, or Firm—Beveridge DeGrandi & Weilacher

[57] ABSTRACT

The object of this invention is a double multichromatic photometer including a single light-source and a single detector, particularly for the determination of chemical and clinical analyses, in which the photometer light comes from a single light-source which radiates along three distinct optical paths that converge onto a single detector; two of the optical paths are the first and the second measuring channels, which are alternatively excluded whereas the third optical path is for reference purposes. An optical collimation assembly and a measurement cuvette are inserted into each of the two measuring optical paths or channels. Within said three optical paths is inserted a rotating drum, said drum holds a number of interference filters, allowing the third reference optical path to pass freely, and inserts one filter at a time into one or the other of the two measuring optical paths. Moreover, a rotating shutter controlled by a motor is also provided for the reference optical path, said shutter coordinately rotates with the filter-bearing drum. An opto-electronic assembly, including printed circuit boards and optical couplers are provided for the selection of filters and the measuring channel.

7 Claims, 5 Drawing Figures

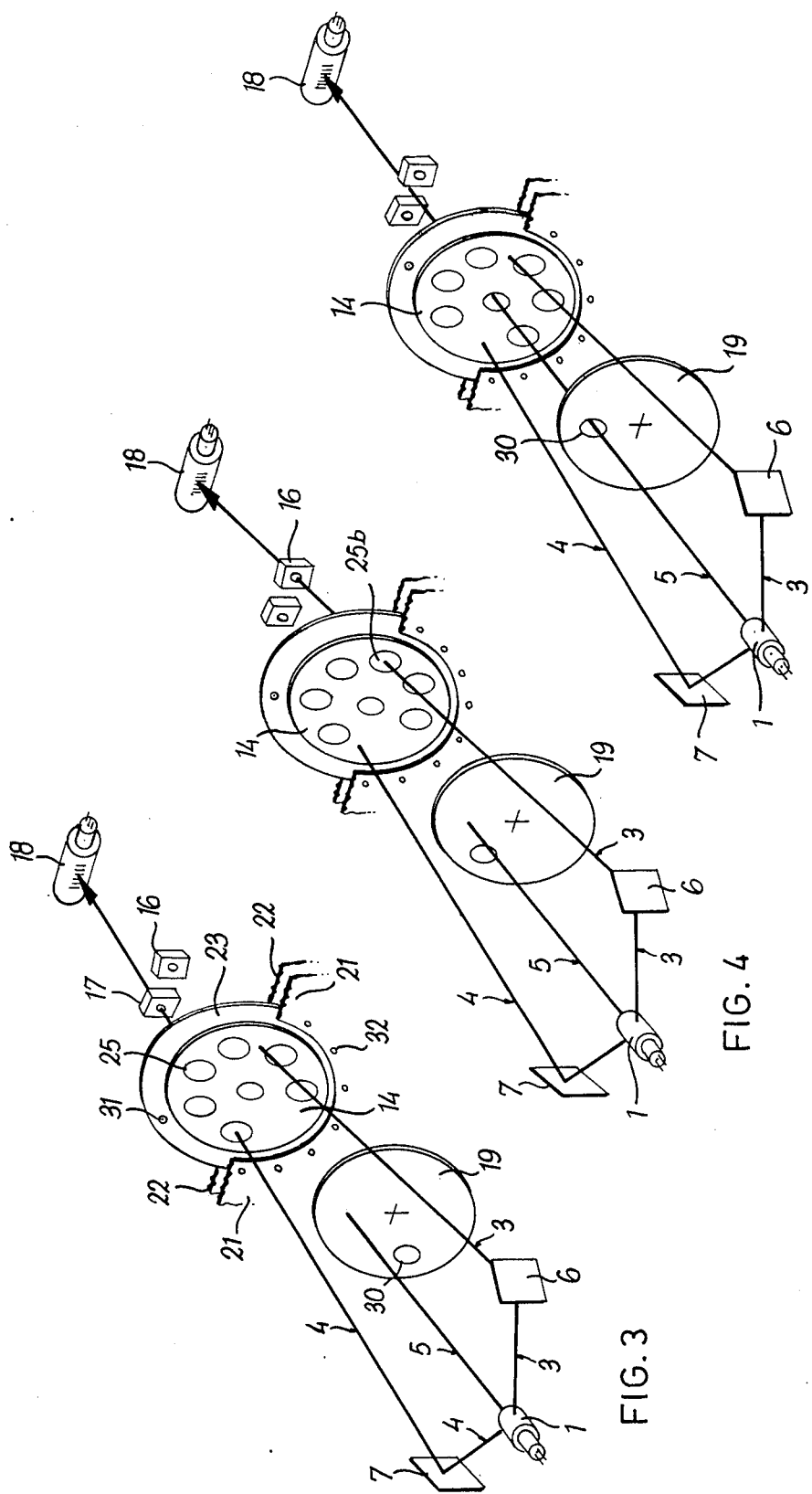

DOUBLE MULTICHROMATIC PHOTOMETER WITH A SINGLE LIGHT-SOURCE AND A SINGLE DETECTOR, PARTICULARLY FOR PERFORMING CHEMICAL AND CLINICAL ANALYSES

DISCLOSURE OF THE INVENTION

The present invention relates to a double multichromatic photometer which is particularly suitable to be incorporated into an automatic system for the determination of chemical and clinical analyses.

More particularly, the object of this invention is a photometer containing two independent measuring cuvettes, in which a single light-source and a single detector are employed, with the possibility of performing analytical measurements with six or more wavelengths.

As will be more evident furtheron, the photometer of the present invention enables also bichromatic determinations or measurements.

From the structural viewpoint, in its present preferred embodiment, the photometer of the invention comprises, in addition to the single light-source and the single detector, also a first and a second measuring channel which are independent and alternatively excluded, and are defined by a first and a second measuring optical path, also comprises a reference or calibration channel which is defined by the third optical path. Said three optical paths converge onto a single detector. The reference optical path is periodically shut by means of an intermittent rotating diaphragm or chopper. A plurality of interference filters, six or more, can be used for the two measuring channels, said filters being selectively introduced into each of the measuring channels. The alternative exclusion action of the measuring channels as well as the insertion action of the interference filters are obtained by means of a rotating drum placed across the two measuring channels, said drum bearing the plurality of interference filters placed circumferentially on said drum in relative positions such that when a filter is inserted into the optical path of one of the channels the other channel is blocked or shut by the drum.

The third optical path passes freely through an axial hole within the drum. The rotating shutter or chopper and the filter-bearing drum are both rotating coordinately by the action of an electrical motor. The rotary position of the disk-bearing drum, which is of utmost importance for identification of the measuring channel and the interference filters employed, is detected by the cooperation of a drilled tab borne by the disk-holding drum and a plurality of light-emitting/light-receiving optical couples that are borne by two opto-electronic circuitry boards. Such identification method can be used also for other operative purposes in other instrumentation, for instance electronic circuitry, which are not part of the present invention.

As pointed out above, the rotation of the rotary shutter disk of the reference path is coordinated with the rotation of the filter-bearing drum so as to enable a periodically passage of the reference beam and to allow a continuous calibration of the apparatus in order to eliminate the drift effects of the light-source and of the detector. Such coordination is to be meant in the mechanical sense, and more precisely it is to be intended in the sense that a single motor drives both the rotary shutter disk and the filter-bearing drum; more particularly, said motor puts in rotation the shutter disk, and the latter puts direct in rotation the filter-bearing drum by means of a pair of crown wheels associated with two such members.

Such coordination is also meant in the sense that, when the calibrating or reference optical path is open, the two measuring channels are blocked or shut by the filter-bearing drum.

Further details and advantages of the invention will become clear following the disclosure by referring to the enclosed drawings which show for illustrative purposes a presently preferred embodiment of the invention without limiting the scope of the same.

In the drawings:

FIGS. 3, 4 and 5 show schematic views of the main component parts of the apparatus in three different operating conditions.

Figure 1:
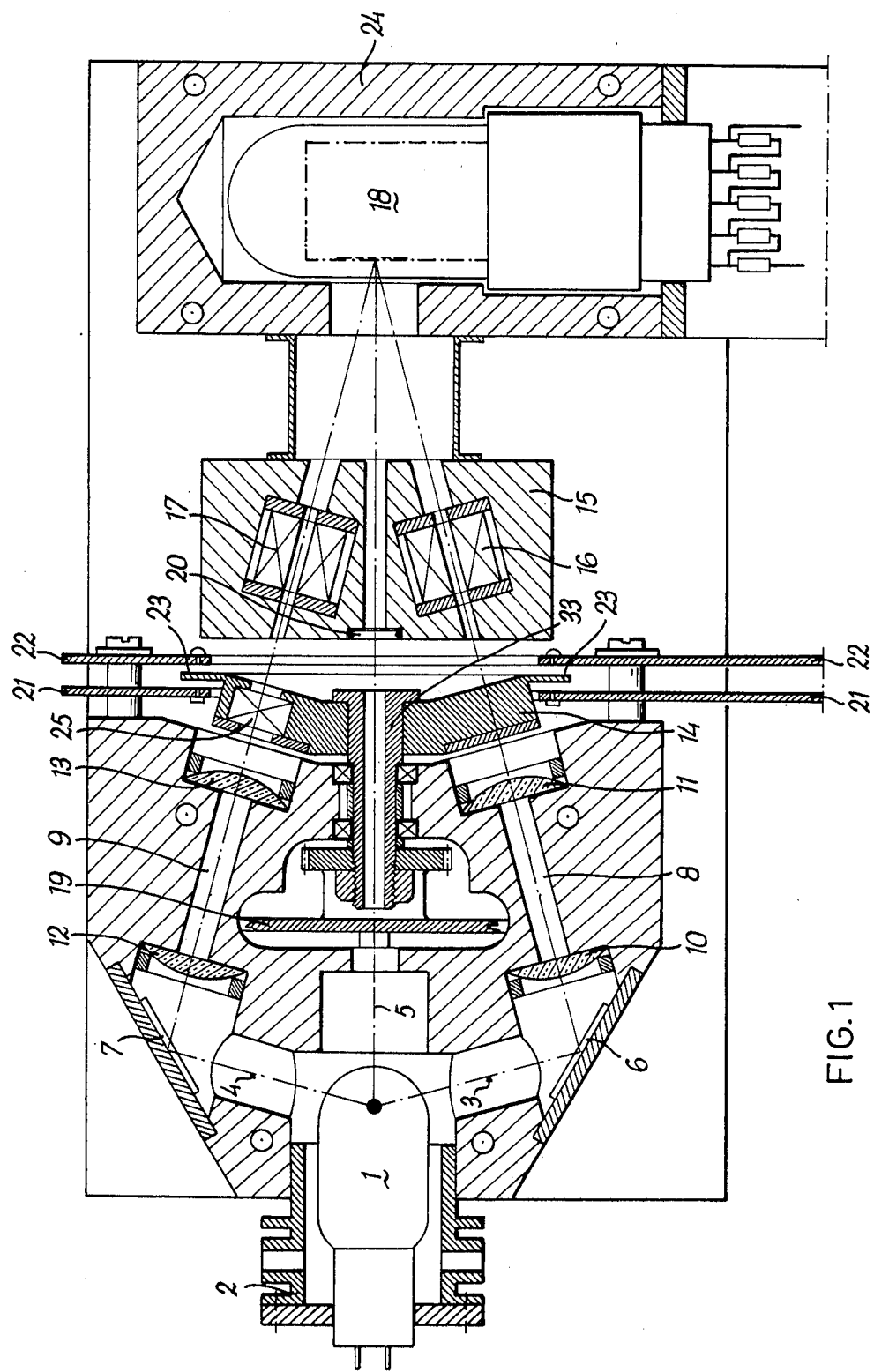
FIG. 1 shows a top plan view approximately taken along the median section, of the double photometer of the present invention.

Referring now to the drawings, and particularly to FIG. 1, the multichromatic double photometer can be seen to comprise a light-source 1 which is housed in a conventional heat-dissipating container 2 for cooling purposes of the light-source itself. Light emitted by the source 1 is radiated along three different and independent optical paths which are perfectly identified by three beams 3, 4 and 5. Paths identified by beams 3 and 4 represent the two principal optical paths for the two measuring channels, whereas the optical path identified by the beam 5 is the reference optical path employed for automatic compensation for drift.

Beams 3 and 4 impinge onto the two mirrors 6 and 7 and are reflected through a 90° angle. Beams 3 and 4 so reflected pass then through the two optical systems 8 and 9, respectively, formed by a pair of plano-convex lenses 10, 11 and 12, 13.

A drum 14 is provided at the output of the two optical systems 8, 9, said drum holds six or more interference filters 25 of different wavelengths arranged circumferentially on it. Such filters are placed in such a way so that, when an interference filter is inserted in one optical path 3 or 4, the other optical path 4 or 3, respectively is blocked or shut by the drum's body 14. The beams 3 or 4 can thus hit one at a time, alternatively the interference filters 25 of drum 14.

As drum 14 rotates continuously, as detailed furtheron it is also employed as a rotary interruptor or chopper.

A block 15 is provided at the exit end of drum 14, said block contains two micro-cuvettes 16 and 17 which are lined up with the optical paths 3 and 4, so that the beams 3 and 4 pass through said micro-cuvettes 16 and 17 and then converge onto the sensitive part of the detector 18.

In order to avoid errors in the analytical measurements due to variations in the light emitted by the light-source 1, for example because of voltage variations, the automatic calibration or offset of the apparatus is provided by means of a direct or reference beam 5 directly impinging onto the detector 18. Thus, employing a well known procedure, the measurements obtained with the two measuring beams 3 and 4 are always referred to a reference measurement done with the direct beam 5, thus automatically eliminating the drift effects.

A drilled disk 19 is provided in the reference beam path 5, said disk operating as a rotary interruptor or chopper, the reference beam 5 passing through its holes and converging onto the sensitive part of detector 8 after passing through the neutral filter 20 assembled within the cuvette-bearing block 15.

It is evident from the disclosure so far given that the apparatus of the invention comprises two measuring channels, and that measurements can be performed with each of said channels at different wavelengths, in correspondence to filters 25 housed within drum 14. The assembly that allows the selection and identification of the channel through which the measurement is carried out as well as the use of a particular filter 25, that is the use of the electronic circuitery assembly (not shown and not a part of the present invention) for the particular measurement to be carried out, comprises two electronic circuit boards 21 and 22 having sequences of optical couplers 32, i.e., optical emitter-receiver couplers, arranged respectively on both sides of the filter-bearing drum 14. Said drum 14 also shows a tab 23, having a small hole 31 in it, peripherally arranged on the same so as to form an optical screen between the optical couplers of the electronic circuit boards 21 and 22 and at the same time to synchronize through said small hole 31 in a selective way the optical coupling between the various emitter-receiver couplers, one at a time. As there are two measuring channels available, the number of optical couplers on the electronic circuit boards 21 and 22 are twice the number of the interference filters 25 provided in the drum 14, so that each filter can be selected for each measuring channel.

The detector 18 is housed in the container 24 which protects the same from interferences due to external light.

FIG. 1 shows a condition in which the measuring channel has been selected with the optical path 4; as a result, the beam 3 is blocked by the solid part of the drum 14 whereas the beam of optical path 4 goes through the filter 25 and reaches the detector 18. In that condition, the reference beam 5 is prevented to pass or is blocked by the shutter disk 19.

Figure 2:
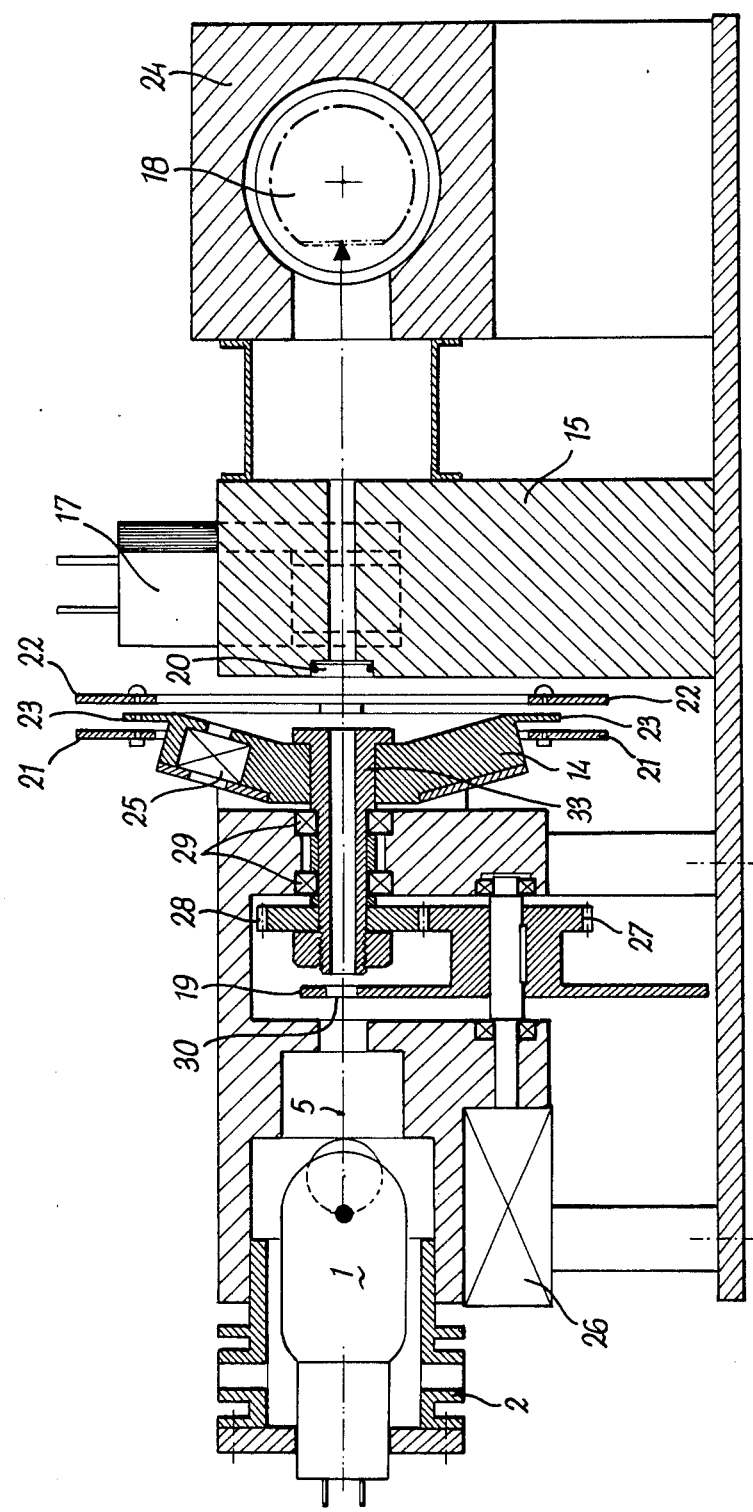
FIG. 2 shows a side view approximately taken in the median section, of the apparatus of FIG. 1.

FIG. 2 shows a cross sectional side view of the apparatus, wherein the beam 5, passing through the hole 30 of the diaphragm 19 and through the neutral filter 20, reaches the detector 18.

With particular reference to FIG. 2, a small motor 26 is provided, on whose output shaft is mounted the assembly of the shutter disk 19 which is integral with a gear 27. Said gear 27 engages gear 28 which is also integral with drum 14. The integral connection between the gear 28 and the drum 14 is obtained through a hallow telescopic shaft 33 assembled on bearings 29; the optical path of the reference beam 5 passing through such hallow shaft.

FIGS. 3, 4 and 5 show schematically, perspectively and in detail the three selection steps of the optical beams 3, 4 and 5. It should be observed that the electronic circuit boards 21, 22 are shown only partially.

FIG. 3 shows the condition in which the measuring beam 3, after being reflected by the mirror 6, is stopped or blocked by drum 14. The reference beam 5 is blocked by the shutter disk 19. The measuring beam 4, after being reflected by the mirror 7 passes through the interference filter 25a of the drum 14, then it passes through the micro-cuvette 17 and reaches the detector 18.

FIG. 4 shows the condition in which the measuring beam 4, after being reflected by the mirror 7, is blocked by drum 14. The reference beam 5 is blocked by the shutter disk 19. The measuring beam 3, after being reflected by the mirror 6, passes through the interference filter 25b of drum 14, then it passes through the micro-cuvette 16 and reaches the detector 18.

FIG. 5 shows the automatic calibration or reference condition, in which both the measuring beams 3 and 4 are reflected by the mirrors 6 and 7 and are blocked by drum 14, whereas the reference beam 5 passes through the hole 30 in the shutter disk or chopper 19 and through the central hole of drum 14, so as to reach directly the detector 18.

A presently preferred embodiment of this invention has been disclosed in the above, but it is clearly understood that those skilled in the art can introduce changes and modifications in the structural details as well as in the reciprocal arrangement of the component parts, without going out of the scope and the spirit of the patent rights of the present invention.

What is claimed is:

1. A multichromatic double photometer particularly suitable for chemical and clinical analyses, wherein the photometer comprises a single light-source;

a single detector;

a first measuring optical path and a second measuring optical path from the light source to the detector for carrying out measurements, each optical path comprising a reflection mirror and a collimating optical assembly;

a reference optical path from the light source which reaches directly the detector after passing through a neutral density filter;

a rotary drum inserted in the first and second measuring optical paths, and bearing a plurality of interference filters arranged in a circular arc so that when one of such filters is inserted into one of the two measuring optical paths, the other measuring optical path is blocked;

a first measurement cuvette in the first measuring optical path between the drum and the detector;

a second measurement cuvette in the second measuring optical path between the drum and the detector;

a rotating shutter disk inserted in the reference optical path and having a hole for passage of a reference beam;

two electronic printed circuit boards having light-emitter receiver optical paths;

a tab integral with the drum and bearing a hole interposed between the two electronic printed circuit boards and cooperating with the boards so as to selectively admit light emitter-receiver optical paths borne by said boards; and motor means for causing said shutter disk, said interference filter-bearing drum and said tab to rotate in a coordinate manner so as to individually select any one of the interference filters.

2. A multichromatic double photometer according to claim 1, wherein said light-source is incorporated within a heat-radiating device for cooling purposes.

3. A multichromatic double photometer according to claim 1, wherein said mirrors are plane mirrors reflecting the light beam through 90°.

4. A multichromatic double photometer according to claim 1, wherein said collimating optical assemblies comprise a pair of plano-convex lenses for each assembly.

5. A multichromatic double photometer according to claim 1, wherein said two measurement cuvettes are arranged within a supporting block in which, in addition to the optical channels for passing the measuring beams, there is also an optical channel for passing the reference beam, such block also supporting said neutral density filter.

6. A multichromatic double photometer according to claim 1, wherein said drum bears six or more interference filters.

7. A multichromatic double photometer according to claim 1, wherein said rotating shutter disk and the filter-bearing drum are so coordinated with each other that, when the hole in the shutter disk is lined up with the reference optical path, both the measuring optical paths are blocked by the filter-bearing drum.

* * * * *